(12) United States Patent
Wornson et al.

(10) Patent No.: US 7,551,274 B1
(45) Date of Patent: Jun. 23, 2009

(54) DEFECT DETECTION LIGHTING SYSTEM AND METHODS FOR LARGE GLASS SHEETS

(75) Inventors: Douglas P Wornson, Northfield, MN (US); Mark M Wornson, Dundas, MN (US); Eric L Hegstrom, Tucson, AZ (US)

(73) Assignee: Lite Sentry Corporation, Dundas, MN (US)

( * ) Notice: Subject to any disclaimer, the term of this patent is extended or adjusted under 35 U.S.C. 154(b) by 199 days.

(21) Appl. No.: 11/680,549

(22) Filed: Feb. 28, 2007

(51) Int. Cl.
*G01N 21/00* (2006.01)

(52) U.S. Cl. .................... 356/239.1; 356/429

(58) Field of Classification Search .............. 356/429, 356/239.1; 250/559.4; 348/86
See application file for complete search history.

(56) References Cited

U.S. PATENT DOCUMENTS

| | | | |
|---|---|---|---|
| 4,223,346 A | 9/1980 | Neiheisel | |
| 4,492,477 A | 1/1985 | Leser | |
| 4,812,740 A | 3/1989 | Shutts | |
| 5,598,262 A | 1/1997 | Jutard | |
| 5,642,198 A | 6/1997 | Long | |
| 5,696,591 A * | 12/1997 | Bilhorn et al. | 356/429 |
| 5,760,907 A | 6/1998 | Basler | |
| 5,870,204 A * | 2/1999 | Chiu et al. | 356/430 |
| 5,887,077 A | 3/1999 | Bongardt | |
| 6,198,529 B1 * | 3/2001 | Clark et al. | 356/237.5 |
| 6,275,286 B1 | 8/2001 | Haubold | |
| 6,359,686 B1 | 3/2002 | Ariglio | |
| 6,437,312 B1 * | 8/2002 | Adler et al. | 250/216 |
| 6,437,351 B1 * | 8/2002 | Smick et al. | 250/492.21 |
| 6,437,357 B1 | 8/2002 | Weiss | |
| 6,616,393 B1 | 12/2002 | Paul | |
| 6,570,651 B1 | 5/2003 | Haubold | |
| 6,628,379 B1 * | 9/2003 | Sudo et al. | 356/237.1 |
| 6,683,695 B1 | 1/2004 | Simpson | |
| 6,704,441 B1 | 3/2004 | Inaguki | |
| 6,757,058 B1 * | 6/2004 | Carman et al. | 356/237.2 |
| 6,985,231 B2 | 1/2006 | Redner | |
| 7,345,698 B2 * | 3/2008 | Abbott et al. | 348/86 |
| 2002/0005892 A1 * | 1/2002 | Herre | 348/86 |
| 2004/0207839 A1 | 10/2004 | Gerstner et al. | |

FOREIGN PATENT DOCUMENTS

| | | |
|---|---|---|
| WO | WO2005/073698 A1 | 8/2005 |
| WO | WO2005/116616 A1 | 12/2005 |
| WO | WO2006/121699 A1 | 12/2005 |

* cited by examiner

*Primary Examiner*—Tarifur Chowdhury
*Assistant Examiner*—Michael Lapage
(74) *Attorney, Agent, or Firm*—Edward Weck

(57) ABSTRACT

A glass defect detection system comprising an apparatus and methods for the real-time inspection for defects in and on transparent sheets, such as a large sheets of glass is disclosed. The defect detection system utilizes a plurality of dark-field illumination systems and bright-field illumination systems and a plurality of baffles. A plurality of imaging devices are deployed to obtain images of transparent sheets. The defect detection system provides uniform lighting capable of equal detection of defects in all orientations and geometries. An image processing system analyzes for defects in and on the transparent sheet.

22 Claims, 11 Drawing Sheets

TOP VIEW

TOP VIEW

DEFECT DETECTION LIGHTING SYSTEM AND METHODS FOR LARGE GLASS SHEETS

BACKGROUND OF THE INVENTION

1. Field of the Invention

The present inventions relate to an inspection system for glass sheet material including coated and non-coated glass.

2. Description of the Related Art

During the manufacture of optically transparent sheets, optical defects and deviations may be produced that render the transparent material imperfect. Optical imperfections are of special concern in glass and plastic sheet applications where optical defects are unacceptable from a quality control standpoint. Optical quality defects include surface imperfections, inclusions and inconsistencies in light transmission or reflection. Scratches, digs, coating anomalies, seeds, stones, chips, particles, tin residue, ripples, distortion, and grind lines are common categories of optical quality defects.

The optical quality of flat glass can be determined through the use a digital imaging device arranged to inspect the glass. This inspection could be done using illumination that reflects off the glass or transmits through the glass. The focus of the digital imaging device is on the glass sheet and the camera generates signals revealing the quality of the glass.

There are problems associated with the inspection of large area substrate such as glass or acrylic for window manufacture. High resolution imaging of discrete defects necessitates multiple cameras and lenses. Multiple imaging devices are typically arranged in series across the width of the substrate, as the substrate traverses a window processing line.

The linear arrangement of multiple cameras necessitated by large substrates makes the lighting of the substrate less than ideal. Uniform and omnidirectional lighting for one camera leads to optical interference with neighboring cameras.

The present invention addresses the fundamental limitations inherent in automated inspection systems for large-area substrate requiring multiple imaging devices arranged in series.

The illumination system used in this new and novel invention produces high contrast images of all types of defects, including very low contrast or very faint defects, and allows detection of a wide variety of defects at high velocity of glass movement.

SUMMARY OF THE INVENTION

Apparatus and methods in accordance with the present inventions may resolve many of the needs and shortcomings discussed above and will provide additional improvements and advantages as will be recognized by those skilled in the art upon review of the present disclosure.

The illumination system used in this glass defect detection system produces high-contrast images and makes possible the detection of a wide variety of defects, including very low contrast or very faint defects, at high velocity of glass movement and assures defect detection. All active optical elements are present on one side of the glass. A series of cameras scans the full width of a glass processing line. Each camera sees both the bright-field and the dark-field, which reduces costs and is more efficient than using two series of cameras. Compared with other systems, the directional qualities of the illumination system produce an exceedingly high-percentage light response from defect features; the same directional qualities make possible the efficient removal from the system of light falling on non-defective areas. With respect to the two types of dark-field lights, their mutually orthogonal orientation and similar directional qualities mean that cross-conveyor scratches yield approximately the same high-contrast response as parallel-conveyor scratches. This important attribute is difficult to achieve in a high-contrast lighting system for glass inspection, and is critical to providing robust automated inspection systems to the industry.

Each camera has semi-collimated lights illuminating its field of view from many positions. The light positions are nearly-matching and opposite in angle of incidence with respect to the camera. This configuration will be referred to as SCNMAI (Semi-Collimated and Nearly Matching Angle of Incidence). This configuration produces an especially large percentage of light scattering back into the camera lens when there is a defect on either surface of the glass. The configuration also insures that where the glass surfaces have no flaws, virtually all the light will bypass the lens on the far side, if it is reflected, or continue straight through the glass; in either case, being semi-collimated, the light can be efficiently managed and removed from the system. This makes for a low "noise floor" against which the defect "signal" is to be resolved. The resulting images have very black surrounds around very bright flaws. The high contrast allows the sensing of very faint flaws which would not be detected by automated inspection systems using alternate means of lighting.

SCNMAI lighting produces superior high-contrast images of flaws. SCNMAI would be impossible to use with more than one camera in the cross-conveyor direction without a system of baffles. Since the cameras are arrayed side by side, each camera would "see" the direct reflection of lights being used to illuminate adjacent cameras' fields of view. The direct reflection would be so intense as to drown out the features of interest in the image. Exposure at the sensor would have to be drastically reduced in order to eliminate blooming, either by reducing the lens aperture or by reducing shutter time. Light received from scratches and other defects would be drastically reduced, and many defects would become undetectable.

The system of baffles allows cross-conveyor lights configured as SCNMAI to perform in the same way as the parallel-conveyor lights. This is particularly important because: 1) without cross-conveyor SCNMAI the light response from defects is highly unequal, depending on whether the defect runs in the parallel-conveyor direction or the cross-conveyor direction; and, 2) it is important that defects appear the same regardless of orientation so that detection thresholds can apply equally to scratches in all orientations.

The system uses an additional, diffuse light source for the purpose of producing a bright-field image in the top half of the camera's field of view. This is done in a way that produces minimal interference with the dark-field imaging described above. The combination of bright-field and dark-field lighting into one field of view allows the detection of a wider variety of defects, including coating flaws as well as digs, scratches, grind errors, internal flaws, and others.

The bright-field image is used additionally for mapping the location and geometry of the glass as it passes through the bright-field side of the image. Here the image of the glass is uniformly white on a uniformly black background. The shape and position of the glass can be determined and the glass can be tracked as it moves through the dark-field. This method of identifying glass versus non-glass areas is quite valuable, both for robustness of image analysis and for speed of processing.

DEFINITIONS

"Camera settings" relate to the camera and include aperture, shutter speed, brightness, gain, sensitivity, offset, gamma compensation, camera filter selection (color or polarization) and camera selection.

"Analysis settings" include sensitivity, offset, intensity thresholds, size thresholds, shape threshold, contrast, software filter settings, texture thresholds and logic sequences. Methods used may include intensity thresholding, either absolute or adaptive. Filters may be used prior to thresholding in order to remove unwanted information or to enhance certain types of features. Shapes of anomalies appear in the image as white "blobs" on a dark background. Standard blob analysis may be used to generate many types of measurements on the blobs including, for example length, width, ratio of perimeter to area and Euler number. The definition of particular defects is a matter of defining ranges or combinations of ranges in these numbers which indicate the presence of that particular defect.

"Lighting settings" include light levels (intensity), selection of specific lights, and polarization or color lighting filters.

The "near-matching angles" are approximately equal and opposite angles of a light assembly versus a camera with respect to the normal to the transparent sheet at the center of the field of view of the camera. The angle associated with the light is normally slightly larger than that of the camera. The difference in angles, while small, is large enough to remove its direct image from the field of view of the camera. The difference is normally in the range of two (2) to twenty (20) degrees.

"Collimated light" is light in which all the light's rays are mutually parallel.

"Semi-collimated light" is light that is shaped into a narrow beam between zero (0) and fifteen (15) degrees.

"SCNMAI" is an acronym meaning a "Semi-Collimated Near-Matching Angle of Incidence" lighting configuration (from definitions above).

"Diffuse light" is light that has the same properties in many directions, with a high degree of scatter or diffusion in transmission or reflection.

"Contrast" is the apparent difference in brightness between features in an image and the neighborhood surrounding the feature.

"Cross-conveyor direction" is perpendicular to the direction of travel of the conveyor (in the plane of the optically transparent sheet).

"Parallel-conveyor direction" is parallel to the direction of travel of the conveyor.

"Step size" is the distance traveled by the sheet between image captures.

The "Dark-field light assembly" provides dark-field illumination.

The "Bright-field light assembly" provides bright-field illumination.

The glass defect detection system according to this invention may be used to inspect optically transparent sheets of various kinds including glass, coated glass, mirrored glass, acrylic, polycarbonate, and other optically transparent or transmissive polymer sheets. Other optically transparent or transmissive polymer sheets include, and are not limited to, polypropylene and polyethylene.

A glass defect detection system according to this invention may analyze glass while being moved on a conveyance system in a production process. The glass moving on the conveyance system may be of the various widths used in commercial glass production. The conveyance system for moving glass may be oriented vertically or horizontally. The conveyance system may employ a belt or rollers or donuts for moving the transparent sheets. The conveyance system may employ an air float system to move the transparent sheets. The conveyance system may be operable at velocities up to 2 m/sec or higher. The conveyance system may transport glass of widths up to 3 m in width, and from 0.5 mm to 25 mm in thickness. Window-sized pieces of glass are large area substrate and may be generally 1 to 2 square meters in size and be transported by the conveyance system.

A glass defect detection system in accordance with the present invention may provide an encoding device. The encoding device may be a digital electronic device used to convert the angular position of a shaft or axle to a digital code, making it a sort of transducer. The encoding device may measure the rate of movement, the acceleration and the deceleration of the conveyance system. The encoding device makes real-time measurements of the incremental movement of the transparent sheet. The encoding device transmits the information about the position of the conveyance system to the trigger circuit.

A glass defect detection system in accordance with the present invention may provide a trigger circuit. The trigger circuit transmits information about the position of the conveyance system to a plurality of cameras. The trigger circuit triggers the cameras to take an image at specific intervals which relate to the precise position of the transparent sheet on the conveyance system.

A glass defect detection system in accordance with the present invention may provide sensors for detecting the presence or absence of a coating on a transparent sheet moving on a conveyance system in a glass production process. Various types of sensors may be used for the detection of coatings on transparent sheets or other transparent materials. These sensors may use laser light, collimated light, semi-collimated light, colored light, or light of a specific wavelength reflected from or transmitted through the coated glass.

A glass defect detection system in accordance with the present invention may provide an illumination system for detecting defects on optically transmissive sheets. It is known to be difficult to detect defects on coated low-E (low-emissivity) glass and uncoated glass with a single lighting scheme. A combination of lighting schemes may be used to detect defects on the coated portion of glass, the edge of the glass where the coating is removed, and on uncoated glass. The combination of lighting may include a bright-field light source and a dark-field light source. The light may be directed at the glass at various angles, wavelengths and intensities. The light may be dispersed, diffuse, semi-collimated, monochromatic or polychromatic. Light sources may include fluorescent, strobe, LED, incandescent and laser light.

The bright-field light is a homogeneous broad diffuse light or area light, in which reflected images of the light source are in the field of view of the camera. Normal non-defective glass in the field of view appears bright. Bright-field illumination may be used to detect defects on the coated glass sheet including coating defects and edge deletion skips. Bright-field illumination may be used for shape recognition, size recognition, and edge definition. Bright-field illumination may be realized by a variety of means including LED, fluorescent, incandescent, strobe, and laser light. The wavelength of the LED lights may be selected to match the wavelength sensitivity of the camera.

Features on the glass which involve changes in reflectivity or diffusion can be observed in the bright-field. Some of these involve non-uniform coating and some involve textures on the glass. Since the purpose of most coatings applied to glass is to change the reflectivity or transmission at particular wavelengths, or to change the diffusion of reflected light, the detection and quantification of non-uniformities in the coating is useful for quality control during the application of coatings. Further, it becomes possible to monitor the results of deliberate removal of coatings, as is often done at the edges of coated glass sheets prior to assembly into IG (insulating glass) units.

Dark field lighting consists of a lighting configuration with respect to the camera such that features of interest are light while the surrounding neighborhood is dark. Normal non-defective glass in the field of view appears black. Reflected images of light sources are out of the field of view of the camera. Conventional dark-field illumination involves propagating light at the transparent sheet at a glancing angle to the surface of the transparent sheet. Said glancing angle varies from 5 degrees to 90 degrees (normal) to the transparent sheet, depending on the manufacturer of the imaging system. In dark-field illumination, only light scattered from the feature or defect is detected by the camera.

The dark-field light sources may be high-intensity LED's, each of whose light is shaped by a lens into a narrow, semi-collimated beam. The LED's and lenses may be assembled side by side into densely packed lines and attached to fixturing bars. Dark field illumination may be realized by a variety of means including LED, fluorescent, incandescent, strobe, and laser light.

Other lighting orientations may be used with this invention. The lights may be opposite in orientation; cross-conveyor and parallel-conveyor. The order of the illumination system and camera in the direction of motion of the transparent sheet may be: 1) cross-conveyor lighting; 2) parallel-conveyor lighting, and; 3) camera. The order of the illumination system and camera may also be: 1) parallel-conveyor lighting; 2) cross conveyor lighting, and; 3) camera. The cross-conveyor light may be on the same side as the camera and not separated by the parallel-conveyor lighting system. The invention may use two or more cross-conveyor light assemblies. The invention may use light assemblies in a grid. The invention may use a larger capture area for the camera, which would necessitate: 1) changing the lenses on the camera, and; 2) increasing the distances of the cameras and the illumination system from the transparent sheet under inspection.

A glass defect detection system in accordance with the present invention may provide an imaging device or camera for the visualization of defects on optically transparent sheets such as glass. The camera may be an electronic imager based on a grid of areas, an electronic area-based detector. The illumination of the transparent sheet may be detected by a CCD (charge coupled device) image sensor. Other image detection sensors may also be used, such as a CMOS (complementary metal oxide semiconductor) image sensor or other image sensors. Line scan cameras may also be used as image detection devices in accordance with the present invention. The "camera settings" for the camera may be adjusted or altered to examine defects in different types of glass including glass with various types of coatings.

The field of view of the camera may be divided, with approximately half of the field of view containing dark field light and half of the field of view containing bright-field light. The bright-field light is a single uniform, diffuse area light. The light is positioned so that when the camera observes it in reflection off the glass, it appears in only half the image. The glass entry region into the camera field of view may be the bright-field and the glass exit regions from the camera field of view may be the dark field. The bright-field examination of glass is suitable for shape recognition, size recognition, edge definition, coating defect detection, edge deletion skips, detection of inclusion defects such as seed and stones and repetitive defects of a similar nature. The dark field examination is suitable for scratches, digs, surface blemishes, edge chips, edge deletion, inclusion defects and repetitive defects of a similar nature.

A glass defect detection system in accordance with the present invention may provide an image processing system for the detection and visualization of defects on a sheet of glass. The image processing system receives a signal from the coating sensor indicating whether the glass is coated or uncoated. If the glass is coated, the image processing system also receives a signal indicating the characteristics of the coating, which can be used in the processing. The image processing system may generate binarized images from the cameras which are processed to determine the location, type and magnitude of defects in or on the sheet of glass. The output from the image processing system may be displayed on a display device. A plurality of high-speed commercial processors may be used in the defect detection system for image processing.

The present invention has been designed to produce images in which, when there is glass present, the appearance of the glass is extremely uniform, black in the dark-field and middle-gray in the bright-field. The detection of defects begins with finding of anomalies in this uniformity. Standard image processing techniques may be used to characterize and ultimately to classify the nonuniformities as particular types and sizes of defects or as non-objectionable anomalies (for example, dust). These techniques generally involve producing a binarized image, and are commonly called blob analysis.

A glass defect detection system in accordance with the present invention may provide an image display. The image processing system receives a signal from the cameras which it processes. The information from the cameras processed by the image processing system may be displayed on an image display. Alternatively an automated device could discard defective transparent sheets.

The method according to the present invention for the optical inspection of a large transparent sheet for the purpose of detecting defects in and on the large transparent sheet, comprises: projecting light onto a transparent sheet from a plurality of lighting sources where each illumination source further comprises a dark-field light assembly comprising a cross-conveyor light assembly and a plurality of parallel-conveyor light assemblies; blocking light reflected from the transparent sheet with a plurality of baffles; receiving light in an imaging device that provides an image of the transparent sheet and transmitting the image of the transparent sheet to an image processing system; and analyzing the image for defects with an image processing system. The step of receiving light in an imaging device includes receiving light from a dark-field field of view and the step of blocking light requires the positioning of baffles relative to the imaging device and the dark-field light assembly so that the reflected image of the illumination source does not appear in the field of view of the imaging device. The step of projecting light, the dark-field light assembly produces a semi-collimated beam positioned at an angle beta to the normal to the transparent sheet and the reflection of the semi-collimated beam from the transparent sheet is located outside the field of view of the imaging device and the imaging device is positioned at angle alpha to the normal to the transparent sheet and the difference in the angle alpha and the angle beta is less than forty-five degrees. The method is also characterized in that the angle alpha and the angle beta are less than thirty degrees from the normal of the transparent sheet. The method is also characterized in that the step of projecting light and the step of receiving light occur on the same side of the transparent sheet. The method is also characterized in that the step of projecting light further comprises projecting light with a bright-field light assembly. The method is also characterized in that the step of projecting light uses a cross-conveyor light assembly and parallel-conveyor light assemblies are linear arrays of LEDs. The method is also characterized in that the step of receiving light uses an imaging device that is an area scan camera.

Other features and advantages of the invention will become apparent from the following detailed description, and from the claims.

BRIEF DESCRIPTION OF THE DRAWINGS

All Figures are illustrated for ease of explanation of the basic teachings of the present invention only; the extensions of the Figures with respect to number, position, relationship and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in various Figures of the drawings, the same numerals designate the same or similar parts. Furthermore, when the terms "top," "bottom," "right," "left," "forward," "rear," "first," "second," "inside," "outside," and similar terms are used, the terms should be understood to reference only the structure shown in the drawings and utilized only to facilitate describing the illustrated embodiments.

DETAILED DESCRIPTION OF THE INVENTION

The figures generally illustrate exemplary embodiments of a glass defect detection systems system 10 or components thereof which include aspects of the present inventions. The particular embodiments of the glass defect detection system 10 illustrated in the figures have been chosen for ease of explanation and understanding of various aspects of the present inventions. These illustrated embodiments are not meant to limit the scope of coverage but instead to assist in understanding the context of the language used in this specification and the appended claims.

The present inventions provide a glass defect detection system 10 and methods for detecting defects in and on transparent sheets using the glass defect detection system 10. The glass defect detection system 10 in accordance with the present inventions may permit the analysis of coated glass and non-coated glass on the same glass production line. The glass defect detection system 10 may be used in the analysis of optically transmissive sheets such as acrylic. The glass defect detection system 10 may be integrated into vertical and horizontal production lines for transparent sheets. The glass defect detection system 10 is configured to analyze defects in and on transparent sheets 14.

Figure 1:
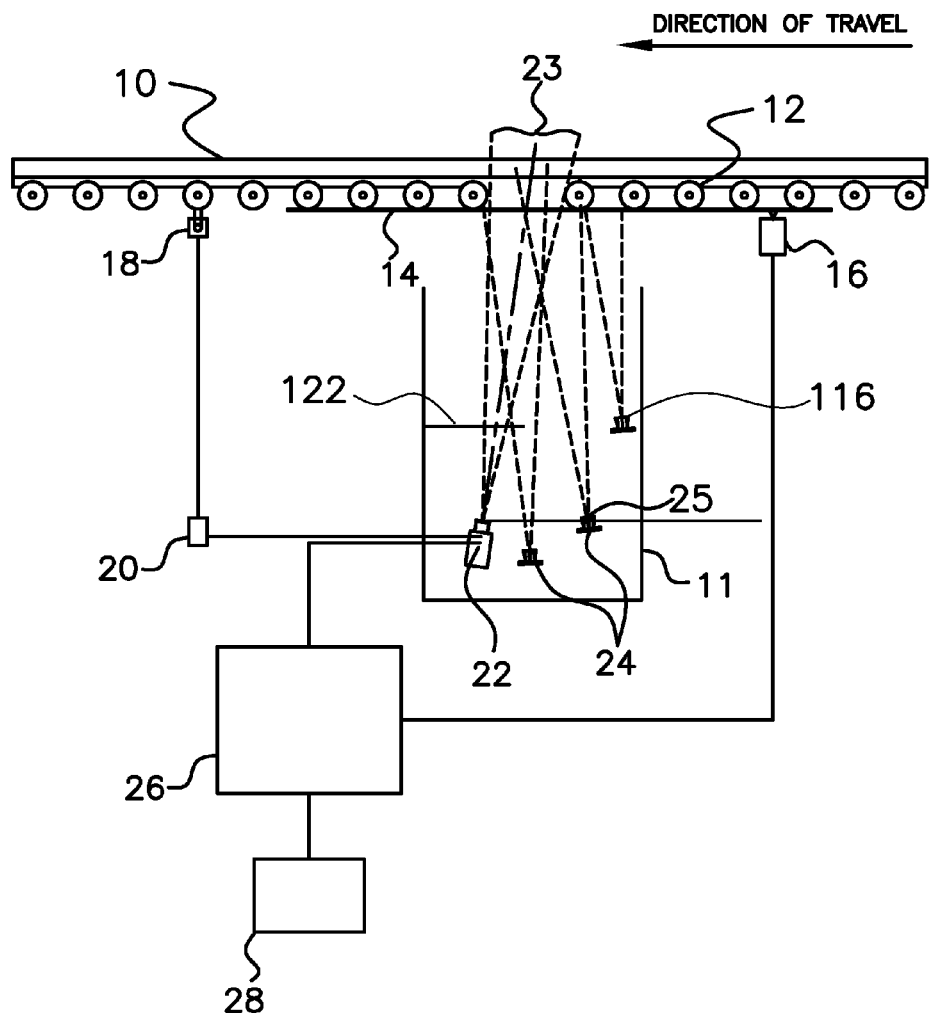
FIG. 1 shows a schematic of a view of the functional components of the glass defect detection system.

As shown in FIG. 1, the glass defect detection system 10 generally includes a sensor 16, an encoding device 18, a trigger circuit 20, a camera 22, an illumination system 24, a diffuse light source light source 116, baffles 122 and an image processing system 26. The glass defect detection systems system 10 may also include a conveyance system 12, an image display 28 and a housing 11. The glass defect detection systems system 10 may include a plurality of cameras 22 and a plurality of illumination systems 24. The glass defect detection system 10 may also include an interface to the conveyance system 12. The conveyance system 12 typically transports a transparent sheet 14 which passes between the conveyance system 12 and a sensor 16. The sensor 16 analyzes reflected light at discrete wavelengths and transmit to the image processing system 26 the type of glass entering the optical inspection. The sensor may also analyze transmitted light. The image processing system 26 adjusts the inspection variables depending on type of coating 15, if any, present on the transparent sheet 14 as measured by the sensor 16 just prior to the transparent sheet 14 passing in front of the camera 22 for inspection. To inspect for defects in or on the transparent sheet 14, it may be illuminated with a plurality of beams of light in the field of view 23 of the camera 22 by the illumination system 24. The encoding device 18 transmits an encoding device signal to the trigger circuit 20 which transmits a trigger circuit signal to the camera 22 to transmit a signal from the camera 22 to the image processing system 26. The image processing system 26 applies inspection variables to the camera signal and transmits an image output signal to the image display 28.

The conveyance system 12 is generally for transporting transparent sheets 14 in a commercial glass production line, as shown in FIG. 1. The conveyance system 12 may use a belt which turns around rollers on which the bottom edge surface of the transparent sheet 14 is conveyed in a manufacturing process. The conveyance system 12 may be like those manufactured by Bystronics or Lisec. Conveyance systems 12 generally known in the art may also be used with these inventions.

The encoding device 18 allows the precise tracking of the location of the transparent sheets 14 along the conveyance system 12, as shown in FIG. 1. The encoding device 18 may be a rotary encoder which pulses 2540 times per revolution of a shaft driving the belt 13 of the conveyance system 12. The encoding device 18 may be like those manufactured by Dynapar. The encoding device 18 tracks the position of the transparent sheet 14. The encoding device transmits a signal to the trigger circuit 20.

The trigger circuit 20 receives a signal from the encoding device 18 and triggers the optical inspection system by transmitting a signal to the camera 22, as shown in FIG. 1. The trigger circuit 20 may trigger the camera 22 to capture an image about every 83.4 mm of movement of the conveyance system 12 or about every 387 pixels in the field of view of the camera 22. The trigger circuit 20 may trigger the camera 22 at various length interval or pixel dimensions to vary the fields of view of cameras camera 22.

The illumination system 24 directs light at the transparent sheet 14 for the detection of defects in and on the transparent sheet 14, as shown in FIG. 1. The illumination system 24 may provide constant illumination from a plurality of lights. The illumination system 24 may use various lights including incandescent, fluorescent, strobe, laser, or narrow bandwidth LEDs. Lumiled LED lights cyan in color (460-540 nm wavelength) may be used. The wavelength of the LED lights is selected to match the wavelength sensitivity of the camera 22. A lens 25 may shape the light beam from the high-intensity LEDs of the illumination system 24 into a narrow, 10-degree semi-collimated beam.

Figure 2:
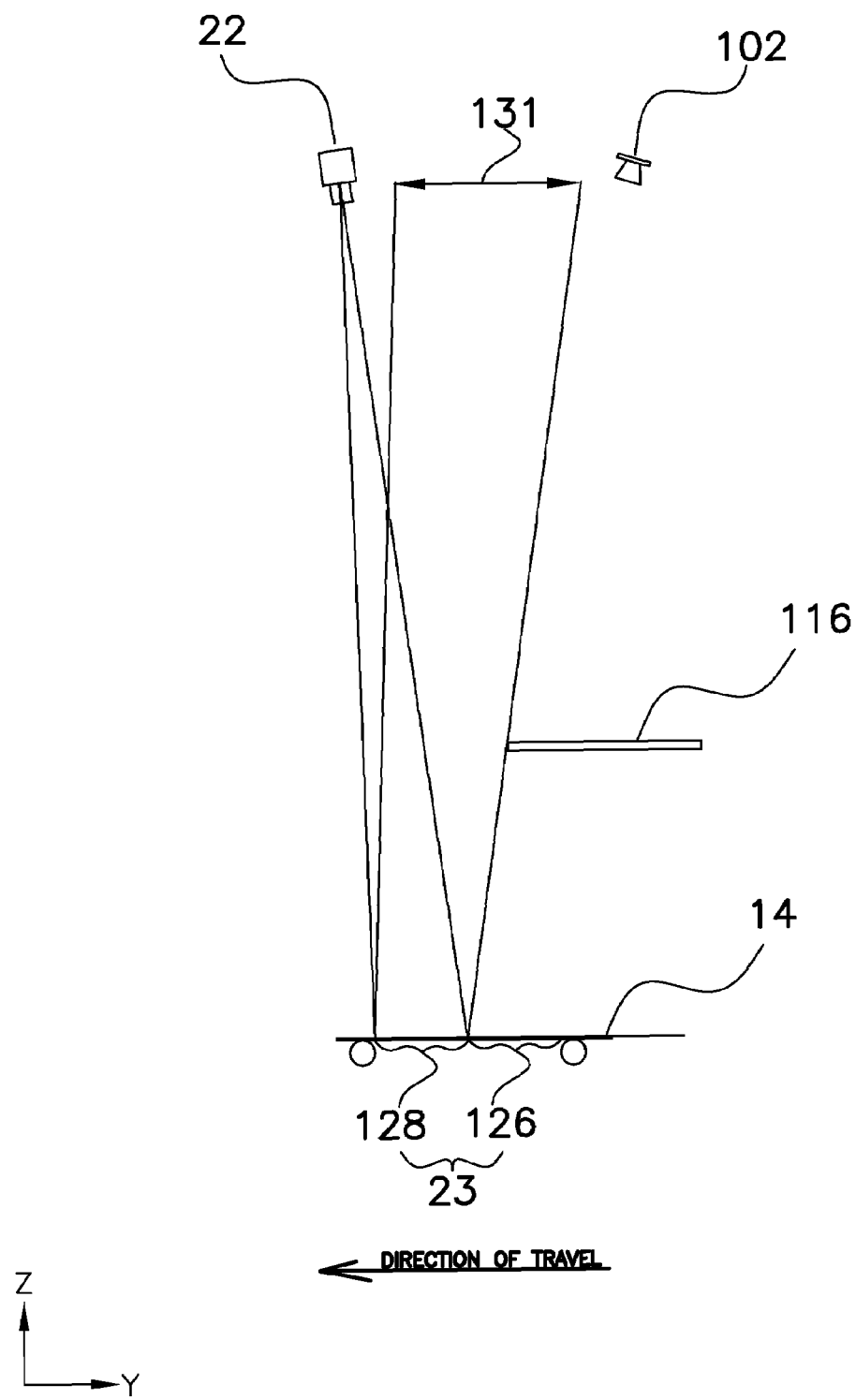
FIG. 2 shows a ray tracing of the light seen by the camera in the dark-field.
Figure 3:
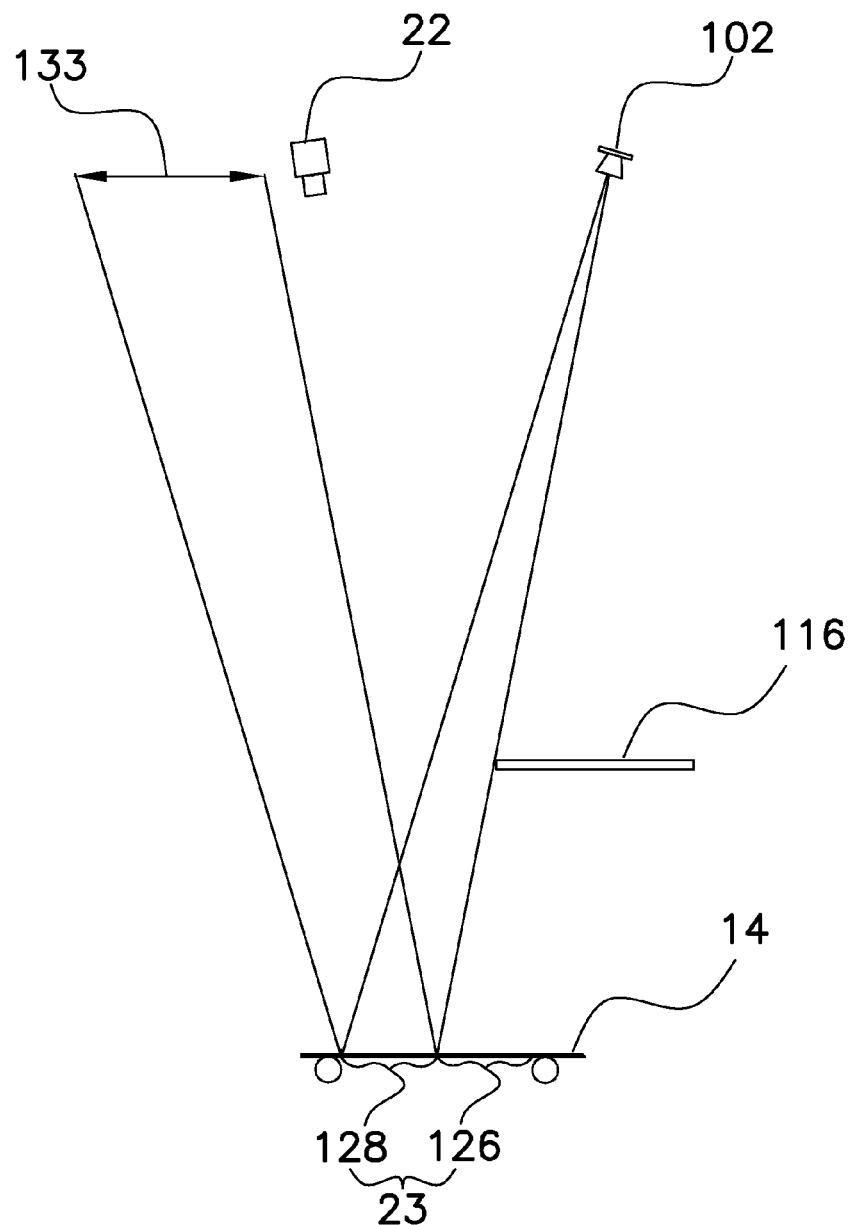
FIG. 3 shows a ray tracing of the directly-reflected light produced by the cross-conveyor light assembly.

The illumination system 24 may be comprised of dark-field illumination and bright-field illumination, as shown in FIGS. 2 and 3. The dark-field and bright-field lighting systems are designed to be optically independent, with no fixed phase relationship between the light from the dark-field and bright-field. The illumination system is entirely enclosed within a light absorbing housing 11.

Dark-field and bright-field light assemblies are generally configured in the following manner. In the dark-field: 1) divide the field of view 23 of each camera 22 into a bright half and dark half; and 2) position the illumination system 24 slightly outside the region seen within the dark-field field of view 128. Where a light according to 1) and 2) above falls within the field of view 23 of another camera 22 or a bright-field field of view 126 of the same camera 22, a baffle 122 is placed to disallow the appearance of the light in that other field of view, adjusting light position slightly if necessary to insure a clear illumination path to the dark-field illumination area, as shown in FIG. 4B. The illumination system 24 must be arrayed in approximately equal measure between parallel-conveyor offsets from dark-field if a bright-field is to be added.

Figure 8:
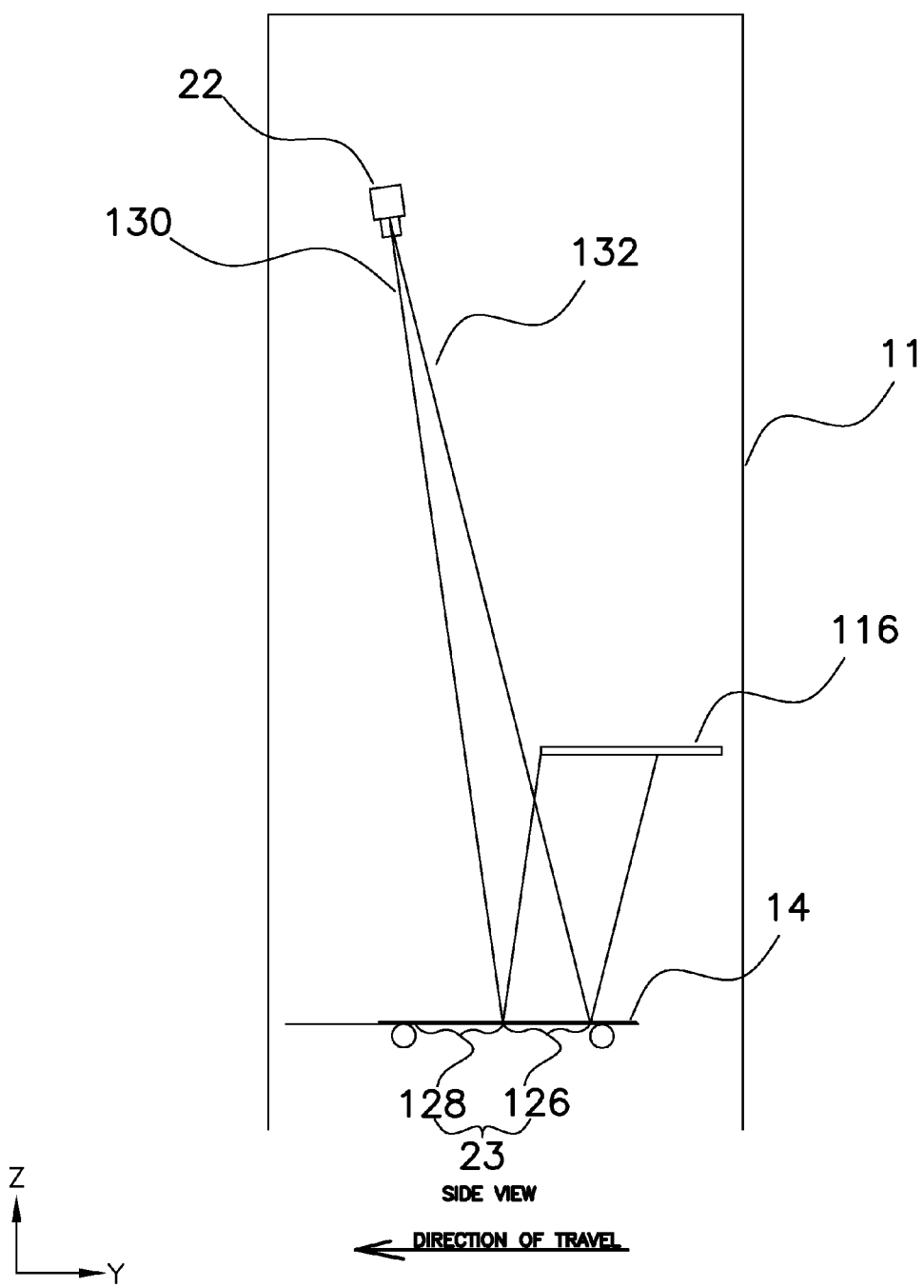
FIG. 8 shows a ray tracing of the light of the bright field illumination reaching the camera lens.

In the bright-field, as shown in FIG. 8, 1) tilt the camera 22 and place a diffuse area light source 116 directed toward the transparent sheet 14 so that the full bright-field sees this diffuse area light source 116 in reflection, and; 2) place a first edge of the diffuse area light source 116 so that it lies on the boundary of the dark-field field of view 128 and the bright-field field of view 126, thus allowing the diffuse area light source 116 also to act to hide the dark-field illumination sources.

A light ray from the light source, like the cross-conveyor light assembly 102, specularly reflected off a transparent sheet 14 without defects, does not enter the lens of the camera 22, as shown in FIG. 3. If light rays are scattered by a defect on the transparent sheet 14, the light rays have a high probability of entering the lens of camera 22. Conversely, the reflected light 133 from a glass sheet 14 without defects is outside the area seen by the camera 22. A higher percentage of the reflected light ends up in the lens of the camera 22 when a slight defect is present on the transparent sheet 14 than in the absence of a defect.

Figure 4A:
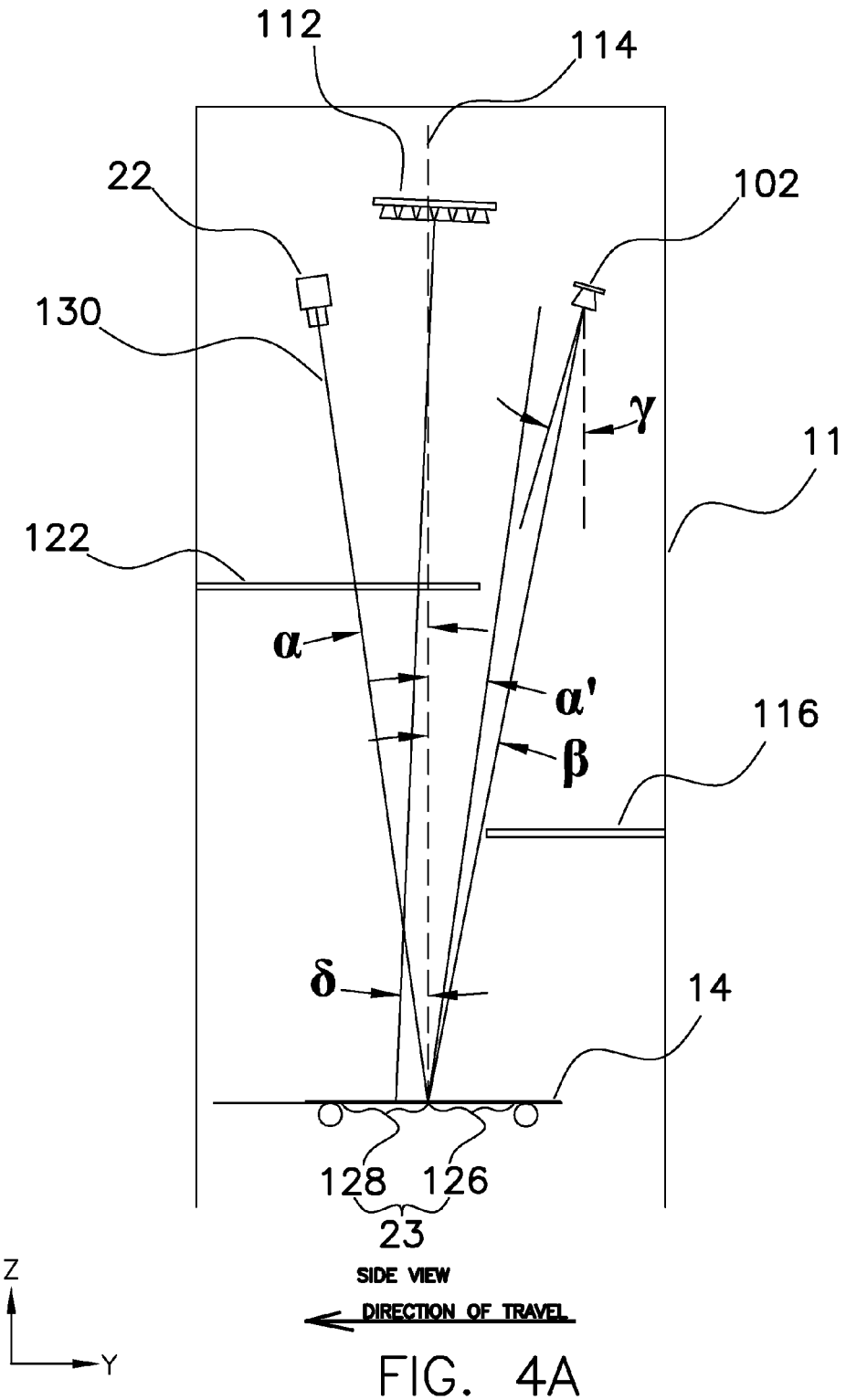
FIG. 4A shows a cross-sectional side view of the illumination system and a camera.
Figure 4B:
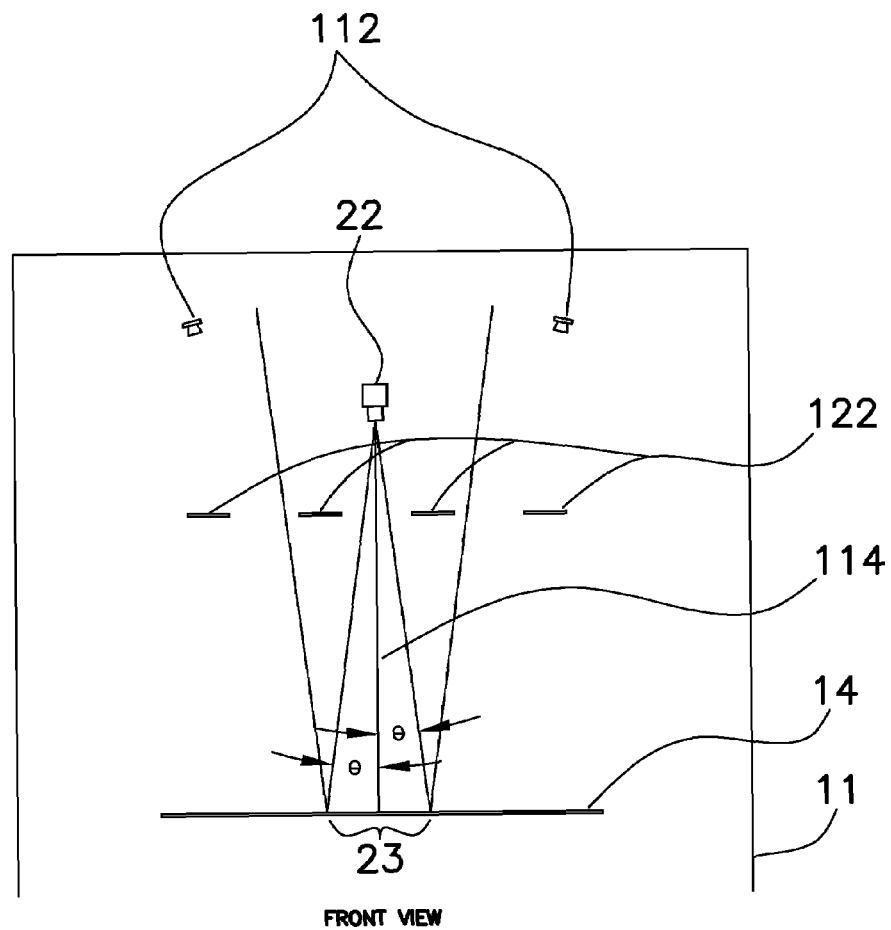
FIG. 4B shows a cross-sectional front view of the illumination system and a camera.
Figure 5:
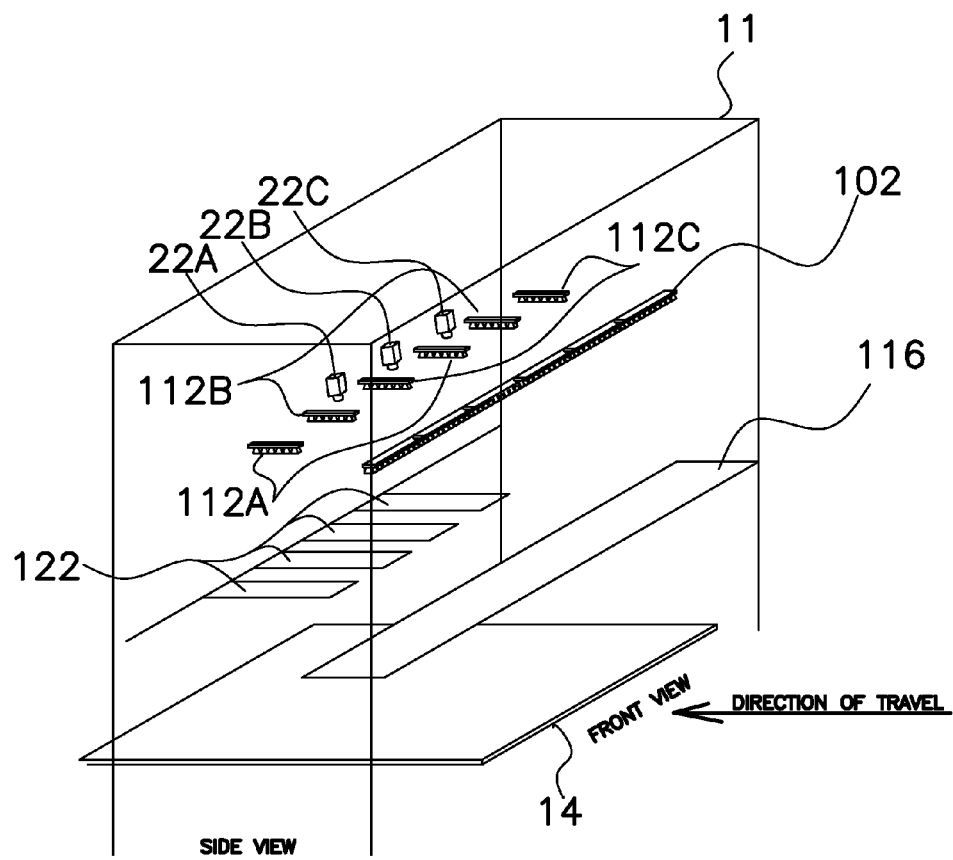
FIG. 5 shows an isometric perspective view of the illumination system and cameras.

As shown in FIGS. 4A and 5, the dark-field illumination is provided by a cross-conveyor light assembly 102 and a plurality of parallel-conveyor light assemblies 112. The cross-conveyor light assembly 102 and the parallel-conveyor light assemblies 112 may be comprised of linear arrays of LEDs. The cross-conveyor light assembly 102 positions the LEDs as a single long row slightly upstream from the field of view 23 of the camera 22. The cross-conveyor light assembly 102 is positioned at angle $\gamma$ to the center of the bright-field field of view 126 of the camera 22.

Figure 9:
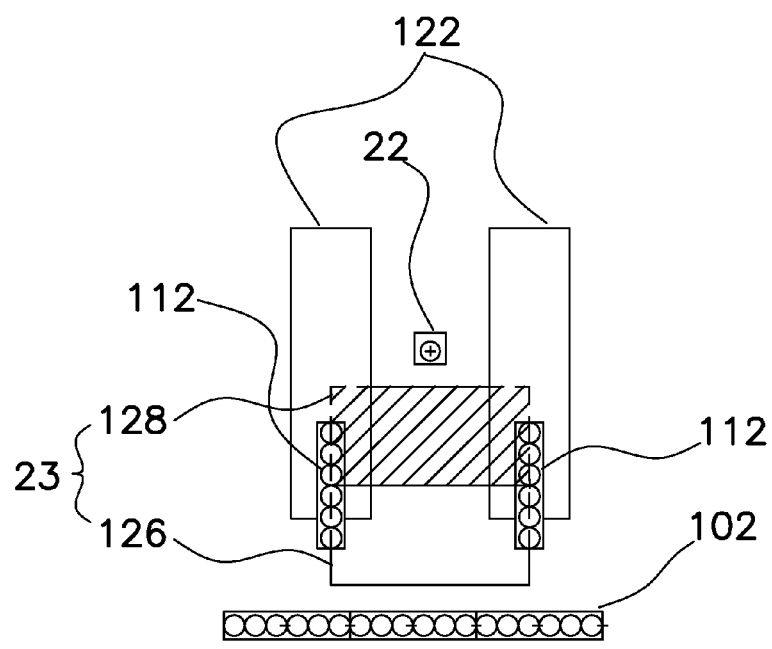
FIG. 9 shows a top view of the camera field of view.
Figure 9:
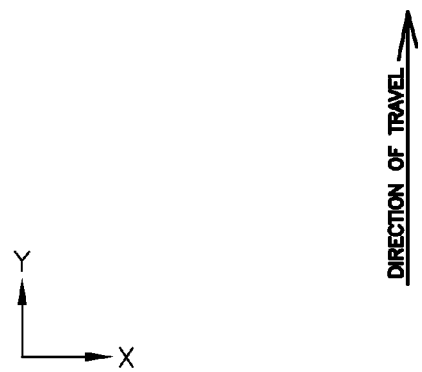

The parallel-conveyor light assemblies 112A, 112B, 112C of LEDs are mounted in pairs to illuminate the dark-field field of view 128 of the pair's assigned camera 22A, 22B, 22C, respectively, as shown in FIG. 5. The camera 22 is mounted downstream of the field of view 23 of the camera 22, as shown in FIG. 9. The camera 22 is directed at the field of view 23 of the camera 22 at angle a to the normal of the glass 114, as shown in FIG. 4A. A specular reflection of light from a transparent sheet 14 would arrive at the camera 22 from angle $\alpha'$ to the normal of the glass 114. The parallel-conveyor light assemblies 112 are disposed in the cross conveyor direction at an angle $\delta$ to the normal of the glass 114, as shown in FIG. 4A.

As shown in FIG. 4A, light from the cross-conveyor light assembly 102 is positioned at the angle $\beta$ to the normal of the glass 114. The angles $\alpha$ and $\beta$ are near matching angles with angle $\beta$ slightly larger than angle $\alpha$ which moves the image of the light reflected off a transparent sheet from the cross-conveyor light assembly 102 out of the dark-field field of view 128 of the camera 22.

There may be a plurality of parallel-conveyor light assemblies 112 and cameras 22, depending on the dimensions of the transparent sheet 14. There may be from two to ten pairs of the parallel-conveyor light assemblies 112 paired with two to ten cameras 22. The parallel-conveyor light assemblies 112 are disposed at an angle delta to the normal of the glass 114, as shown in FIG. 4A.

As shown in FIGS. 4A, 4B, 5 and 7, the use of a plurality of parallel-conveyor light assemblies 112 and cameras 22 necessitates the use of baffles 122. Baffles 122 are required to prevent reflected light from the adjacent pairs of parallel-conveyor light assemblies 112 from entering the field of view 23 of the adjacent camera 22.

As shown in FIGS. 4A, 4B, 5 and 7, the location of the camera 22 and cross-conveyor light assembly 102 and parallel-conveyor light assemblies 112 relative to the camera field of view 23 are important to minimize keystone distortion and to allow optimum focus of the camera 22 over the field of view 23. The distance G of the illumination system 24 from the transparent sheet 14 is about 1.3 meters, as shown in FIG. 6.

Figure 6:
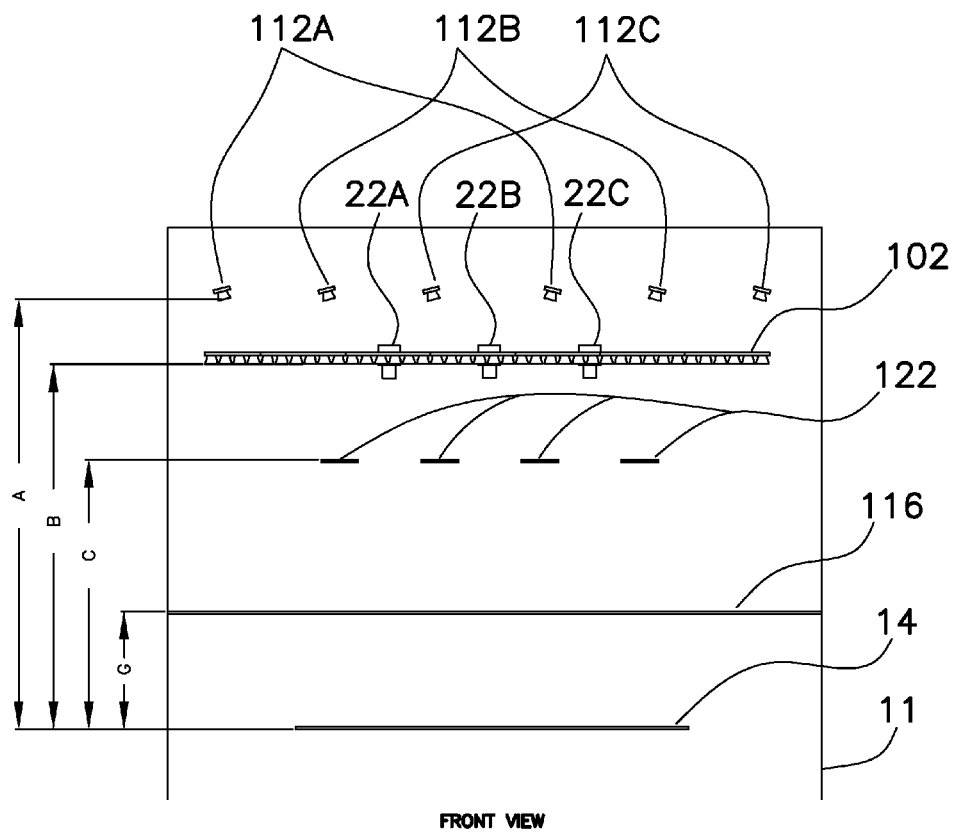
FIG. 6 shows a cross-sectional front view of the illumination system and cameras.

The parallel-conveyor light assemblies 112 are separated from the transparent sheet by a distance of A, about 130 cm, as shown in FIG. 6. The cross-conveyor light assembly 102 is separated from the transparent sheet by a distance of B, about 145 cm, as shown in FIG. 10. The baffles 122 are separated from the transparent sheet by a distance of C, about 123 cm, as shown in FIG. 6.

Figure 7:
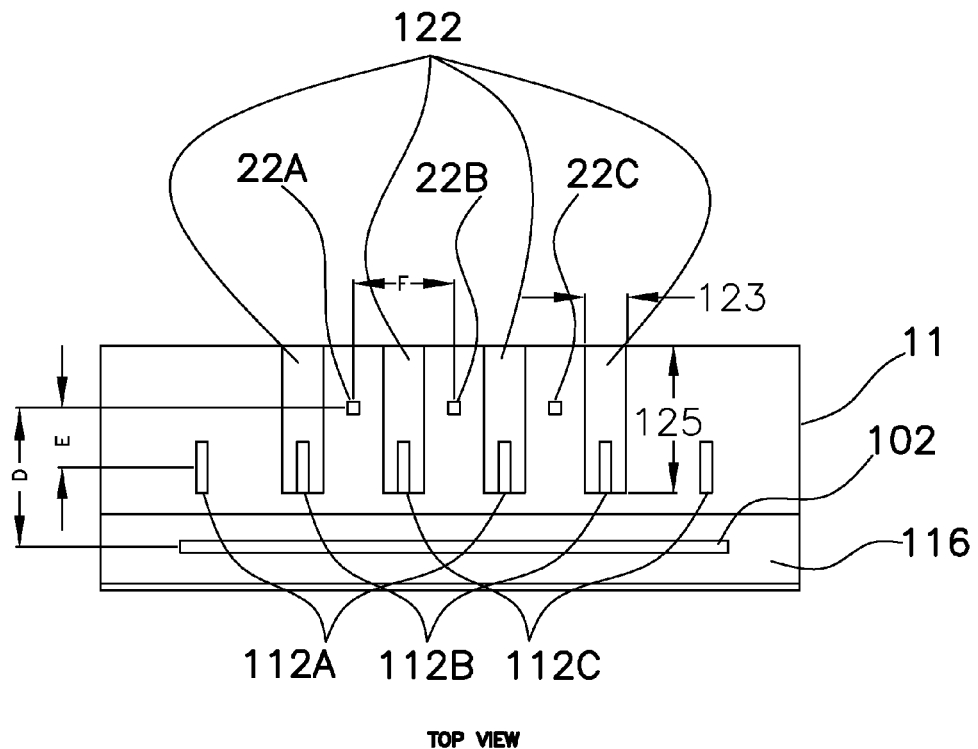
FIG. 7 shows a cross-sectional top view of the illumination system and cameras.

The cameras 22A, 22B and 22C are separated from each other by a distance F, about 30 cm apart, as shown in FIG. 7. The cameras 22 and the parallel-conveyor light assemblies 112 are separated by a distance E, about 22 cm, as shown in FIG. 11. The cameras and the cross-conveyor light assembly 102 are separated by a distance D, about 44 cm, as shown in FIG. 7.

Referring to FIG. 7, there is approximately 20 cm between the baffles 122 which have a baffle width 123 of about 10 cm and a baffle length 125 of about 30 cm. The baffle length 125 is dependent on the length of the parallel-conveyor light assemblies 112A, 112B and 112C. The baffle width 123 is dependent on the disposition of the cameras 22 and parallel-conveyor light assemblies 112A, 112B and 112C and the cross conveyor light assembly 102. The size of the baffle 122, the angles $\alpha$ and $\beta$, the distance from the illumination system 24 to the baffles 122, and the baffle width 123 are all interrelated, as shown in FIGS. 4A and 7. Reducing the angles $\alpha$ and $\beta$, increases the distance between the transparent sheet 14 and the illumination system 24 and the baffles 122 and bright-field lighting.

Figure 10A:
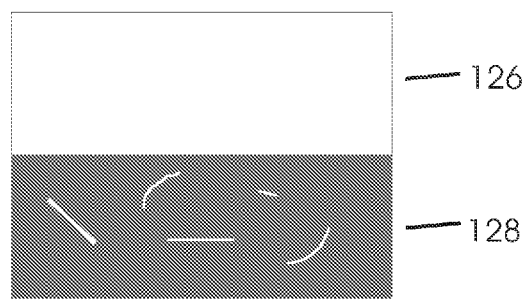
FIG. 10A shows a schematic representation of defects detected in the dark-field.
Figure 10B:
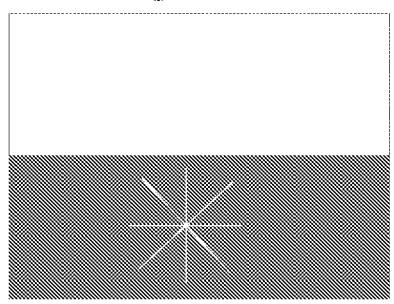
FIG. 10B shows a schematic representation of a scratch pattern under diffuse lighting.
Figure 10C:
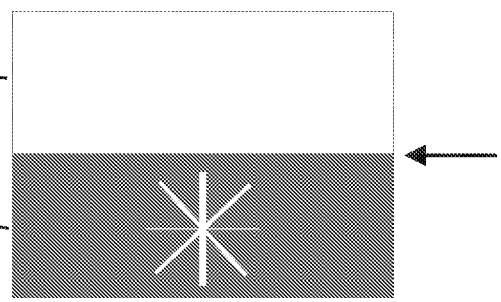
FIG. 10C shows a schematic representation of a scratch pattern with illumination from the parallel-conveyor light assemblies only.
Figure 10D:
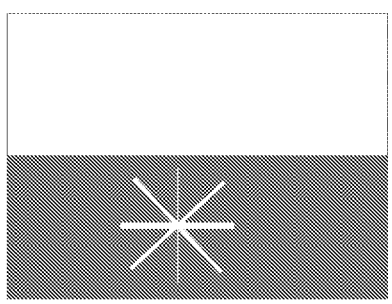
FIG. 10D shows a schematic representation of a scratch pattern with illumination from the cross-conveyor light assembly only.

The use of diffuse light for the detection of many of the most common types of defects yields a poor signal to noise ratio resulting in a low-contrast image in the camera 22 or often an invisible defect, as shown in FIG. 10B. Illumination of a cross-conveyor scratch on a transparent sheet 14 with only light from the parallel-conveyor light assembly 112 results in a low contrast, nearly invisible image of the scratch in the camera 22, as shown in FIG. 10C. Illumination of a parallel-conveyor scratch on a transparent sheet 14 with only light from the parallel-conveyor light assembly 112 results in a high contrast, well defined image of the scratch in the camera 22, as shown in FIG. 10C. Illumination of a cross-conveyor scratch on a transparent sheet 14 with only light from the cross-conveyor light assembly 102 results in a high contrast, well defined image in the camera 22, as shown in FIG. 10D. Illumination of a parallel-conveyor scratch on a transparent sheet 14 with only light from parallel-conveyor light assembly 102 results in a nearly invisible image in the camera 22, as shown in FIG. 10D.

Figure 10E:
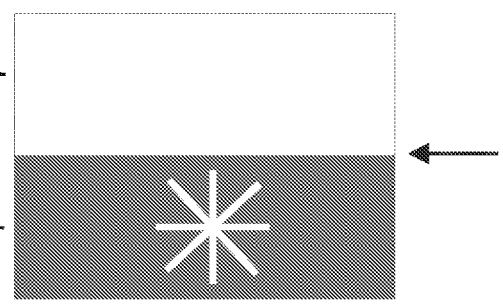
FIG. 10E shows a schematic representation of a scratch pattern with illumination from both the parallel-conveyor light assemblies and the cross-conveyor light assembly.

As shown in FIG. 10E, illumination of scratches in all orientations on a transparent sheet 14, with light from both parallel-conveyor light assemblies 112 and the cross-conveyor light assembly 102, results in a high contrast image and a higher detection of defects on a transparent sheet 14. The intensity of light at the scratch is greatest with the use of light from both parallel-conveyor light assemblies 112 and the cross-conveyor light assembly 102. This results in a uniformity of response of the detection system to scratches in all orientations from parallel-conveyor to cross conveyor. There is a consistent contrast for scratches of all orientations. This consistent contrast allows the use of a single number tuning value as an analysis setting.

As shown in FIG. 8 lighting for the bright-field field of view 126 of the camera is from a diffuse area light source 116. Fluorescent lights or incandescent lights may provide the diffuse area light. The diffuse area light source 116 is positioned so that when the camera 22 observes the light in reflection off the transparent sheet 14 it appears in only half the camera image. The light for the bright-field provided by the diffuse area light source 116 is much weaker in intensity than the light for the dark-field. In order for the camera 22 to see the bright-field light source, it is necessary to direct the camera at an angle a relative to the field of view 23, as shown in FIG. 4A.

As shown in FIG. 1, the camera 22 records an image of the transparent sheet 14 as it passes through the light produced by an illumination system 24. The camera 22 receives an input signal from the trigger circuit 20 telling the camera when to capture an image. The camera 22 may be an area scan image device or line scan image device, either utilizing CMOS image sensors or CCD image sensors. There may be a plurality of cameras 22A, 22B, 22C recording images of transparent sheets 14 as the transparent sheets 14 move along the conveyance system 12, as shown in FIG. 5. The camera 22 takes multiple images and transmits these images to the image processing system 26. The image processing system 26 combines multiple images from the 22A, 22B, 22C to create a single composite image of the transparent sheet 14 as it is passing by the cameras 22A, 22B, 22C. The camera 22 may be an area scan camera manufactured by Point Grey Research with a field of view of 1600×1200 pixels. Other area scan cameras 22, of the area scan or line scan type, known to those of skill in the art may be used with the present inventions. The "camera settings" for the camera 22 may be adjusted or altered to examine defects on or in different types of transparent sheets 14 including glass with various types of coatings 15.

As shown in FIG. 9, the field of view of the camera 22 may be divided into two areas, which may be equal in area. The first area of the field of view 23 contains dark-field lighting and the second area of the field of view 23 contains bright-field lighting. The bright-field light is a single uniform, diffuse area light. LED lights are used to illuminate a white acrylic sheet which diffuses light over the transparent sheet 14 as it passes through the field of view 23.

The bright-field light is positioned so that when the camera 22 observes the reflection off the transparent sheet 14, the bright-field reflection appears in only half the image, as shown in FIG. 9. Features on the transparent sheet 14 which involve changes in reflectivity or diffusion can be observed in the bright-field. Some of these involve a coating 15 of a non-uniform nature and some involve textures on the transparent sheet 14.

As shown in FIG. 1, the camera 22 and the illumination system 24 are enclosed in a housing 11. The housing 11 reduces the amount of stray light that may be directed at the transparent sheet 14 from the room during the inspection process. The housing 11 also provides physical protection from other elements in the production environment.

As shown in FIG. 1, image processing system 26 receives and processes signals from the sensor 16 and receives and processes signals from the camera 22. The image processing system 26 comprises a plurality of microprocessors of the Intel Xeon type. The image processing system 26 receives the output from the sensor 16 indicating the presence or absence of coating 15 on a transparent sheet 14, and, if a coating 15 is present on a transparent sheet 14, the type of coating 15 on the transparent sheet 14. Based on the output signal from the sensor 16, the sample profile, the image processing system 26 adjusts the camera settings for the camera 22. If the sample profile from the sensor 16 indicates that the transparent sheet 14 has no coating 15, the image processing system 26 transmits a signal to the camera 22 to set the shutter speed to be about 0.0007 seconds and signal gain to be about −3.0 dB and gamma to be about 3.5. If the sample profile from the sensor 16 indicates that the transparent sheet 14 has a coating 15, the image processing system 26 transmits a signal to the camera 22 to set the shutter speed to be about 0.0008 seconds and the signal gain to be about 1.5 dB and gamma to be about 1.0. The image processing system 26 also receives a signal or image from the camera 22. The image includes both a dark-field field of view 128 and a bright-field field of view 126, as shown in FIG. 9.

Inspection variables within the image processing system 26 are adjusted according to the signal received from the sensor 16, the sample profile. The signal from the camera 22 is analyzed at different levels of contrast based on the signal received from the sensor 16 which changes the sensitivity of defect detection in and on transparent sheets 14. Standard image processing techniques may be used to characterize and classify the non-uniformities as particular types and sizes of defects or as non-objectionable anomalies (for example, dust). Standard image processing techniques are embodied in software available, for example, from Open Source Computer Vision Library, Matrox MIL or Cognex Vision Pro. Image processing techniques generally involve producing a binarized image. Methods used for image processing may include intensity thresholding, either absolute or adaptive. Filters may be used prior to thresholding in order to remove unwanted information or to enhance certain types of features. Shapes of anomalies appear in the image as white "blobs" on a dark background. Standard blob analysis may be used to generate many types of measurements, both individual and composite, on the blobs including, for example, length, width, ratio of perimeter to area, Euler number and blobs per square inch. Ranges or combinations of ranges of these measurements may be defined to indicate the presence of a particular defect.

Inspection variables within the defect detection system 10 can be adjusted or altered to examine defects in different types of transparent sheets 14 including various types of coatings 15 on the transparent sheet 14. The defect detection system 10 adjustable inspection variables may include shape requirements, geometric analysis of defects, quality thresholds for defects, contrast, absolute brightness, image processing parameters, and descriptions of norms for a variety of types of glass under analysis. The results from image analysis in the image processing system 26 are displayed on an image display 28 so that the user can decide to accept or reject the transparent sheet 14, as shown in FIG. 1. Alternatively an automated device could discard defect transparent sheets 14.

FIG. 1 illustrates a schematic of a glass defect detection system 10 transparent sheets 14 are transported by a conveyance system 12 along an IG unit assembly line at speeds of up to 2 m/sec or more. The direction of transport of the transparent sheet 14 by the conveyance system 12 is shown in FIG. 1 from right to left. The encoding device 18 tracks the location of the transparent sheet 14 along the conveyance system 12. The encoding device 18 transmits a signal to the trigger circuit 20. The trigger circuit 20 receives the signal from the encoding device 18 and transmits a signal to the camera 22. The trigger circuit 20 triggers the cameras 22 to capture an image about every 83.44 mm of movement of the conveyance system 12 or about every 387 pixels in the field of view 23 of the camera 22.

The conveyance system 12 transports a transparent sheet 14, from right to left in FIG. 1, and the transparent sheet 14 first passes in the light path of a sensor 16. The sensor 16 sends a signal to the image processing system 26, the sample profile, indicating whether the transparent sheet 14 has a coating 15 and if so what type of coating 15 is present on the transparent sheet 14. The image processing system 26 transmits a signal to the camera 22 adjusting the "camera settings." If the output signal from the sensor 16 indicates that the transparent sheet 14 does not have a coating 15, the image processing system 26 transmits a signal to the camera 22 to set the shutter speed to be about 0.0007 seconds and signal gain to be about −3.0 dB and gamma to be about 3.5. If the output signal from the sensor 16 indicates that the transparent sheet 14 has a coating 15, the image processing system 26 transmits a signal to the camera 22 to set the shutter speed to be about 0.0008 seconds and the signal gain to be about 1.5 dB and gamma to be about 1.0.

As shown in FIG. 1, the camera 22, the illumination system 24, the baffles 122 and diffuse light source 116 are enclosed in housing 11. The housing 11 reduces the amount of stray light that may be directed at the transparent sheet 14 from the room during the inspection process. The housing 11 also provides physical protection from other elements in the production environment. The camera 22 captures images of the transparent sheet 14 about every 83.44 mm of movement of the conveyance system 12 or about every 387 pixels in the field of view 23 of the camera 22. These images captured by the camera 22 are transmitted to the image processing system 26. Standard image processing techniques including those embodied in software from Open Source Computer Vision are used. Image processing uses absolute or adaptive intensity thresholding. Standard blob analysis generates measurements including length, width, ratio of perimeter to area and Euler number. The images are then output to the image display 28.

FIG. 2 illustrates a ray tracing of the light seen directly by the camera 22 in the dark-field field of view 128. FIG. 2 illustrates the alignment of the camera 22 relative to the bright-field field of view 126, the dark-field field of view 128, the cross-conveyor light assembly 102 and the diffuse area light source 116. The camera 22 is aligned so that the lower portion of the camera 22, the dark-field portion, images the dark-field field of view 128. The reflected image area 131 captured by the camera 22 is downstream, in the direction of travel of the transparent sheet 14, from the light projected by the cross-conveyor light assembly 102.

FIG. 3 illustrates a ray tracing of a light ray from the cross-conveyor light assembly 102 specularly reflected off a transparent sheet 14 without a defect and not entering the camera 22. The position of diffuse area light source 116 is shown relative to the light rays from the cross-conveyor light assembly 102. The directly reflected light 133 from a transparent sheet 14 without defects is outside the area seen by the camera 22. Conversely, if light rays are scattered by a defect on the transparent sheet 14 the light rays have a comparatively higher probability of entering the camera 22. A higher percentage of the reflected light ends up in the camera 22 when a slight defect is present on a transparent sheet 14.

FIG. 4A illustrates a cross-sectional side view of the Y-Z plane of the illumination system 24 relative to the camera 22, the transparent sheet 14 and the bright-field field of view 126 and the dark-field field of view 128. The camera 22 is positioned to the field of view 23 of the camera 22 along the angle $\alpha$ to the normal of the glass 114, intersecting at the center of the field of view 23. The cross-conveyor light assembly 102 is disposed at an angle $\beta$ to the normal of the glass 114. The angle $\alpha$ is an equal and opposite angle to $\alpha$, the direct reflection about the normal of the glass 114. The angles $\alpha'$ and $\beta$ are near matching angles with angle $\beta$ slightly larger than angle $\alpha'$, and moving the image of the cross-conveyor light assembly 102 out of the dark-field field of view 128 of the camera 22. The parallel-conveyor light assembly 112 is positioned along an angle $\delta$ to the normal of the glass 114. The angle $\gamma$ is the angle of disposition between the central axis of the beam from the cross-conveyor light assembly 102 and the normal of the glass 114. The angle $\delta$ and the angle $\gamma$ ensure the camera 22 does not see direct reflections off the transparent sheet 14 from the dark-field lighting. The angles $\alpha, \alpha'$ are between one and thirty degrees and about eight degrees in a preferred embodiment. The angle $\beta$ is between one and thirty degrees and about eleven degrees in a preferred embodiment. The angles $\delta$ and the angle $\gamma$ are between one and thirty degrees and about six and sixteen degrees, respectively, in a preferred embodiment.

FIG. 4B illustrates a cross-sectional front view of the X-Z plane of the parallel-conveyor light assembly 112 relative to the camera 22, the baffles 122, the transparent sheet 14 and the field of view 23. The camera 22 is positioned along the normal of the glass 114. The camera 22 sees from a first edge of the field of view 23 to a second edge of the field of view 23. The camera 22 captures an image of angle 2θ from the center of the camera 22. The baffles 122 prevent light from the parallel-conveyor light assembly 112 from entering the field of view of the camera 23. The camera 22 is positioned along angle θ to the normal of the glass 114 so that it does not see direct reflections off the transparent sheet 14 from the parallel conveyor light assemblies 112. The angle θ is between one and thirty degrees and about eight degrees in a preferred embodiment.

FIG. 5 illustrates an embodiment of the present invention with three cameras (22A, 22B, and 22C) and shows the relative positioning of three cameras (22A, 22B, and 22C), the cross-conveyor light assembly 102, three pairs of parallel-conveyor light assemblies (112A, 112B, and 112C), the baffles 122, and the diffuse area light source 116 relative to the transparent sheet 14 being transported along the conveyance system 12. A housing 11 completely encloses the three cameras (22A, 22B, and 22C), the cross-conveyor light assembly 102, the three pairs of parallel-conveyor light assemblies (112A, 112B, and 112C), the baffles 122, and the diffuse area light source 116 and prevents ambient light from entering the housing 11.

FIG. 6 illustrates an embodiment of the present invention with three cameras (22A, 22B, and 22C) and three pairs of parallel-conveyor light assemblies (112A, 112B, and 112C) as viewed from the front of the glass defect detection system 10 with the transparent sheet 14 moving along the Y-axis into the paper. FIG. 6 shows the relative positioning of three cameras (22A, 22B, and 22C), the cross-conveyor light assembly 102, three pairs of parallel-conveyor light assemblies (112A, 112B, and 112C), the baffles 122, and the diffuse area light source 116 relative to the transparent sheet 14 being transported along the conveyance system 12. The pairs of parallel-conveyor light assemblies (112A, 112B, and 112C) are separated by distance A from the transparent sheet 14. The distance A is between 90 cm and 195 cm, and about 130 cm in a preferred embodiment. The cross-conveyor light assembly 102 is separated from the transparent sheet 14 by distance B. The distance B is between 100 cm and 220 cm and about 145 cm in a preferred embodiment. The baffles 122 are separated from the transparent sheet 14 by the distance C. The distance C is between 85 cm and 185 cm and about 123 cm in a preferred embodiment. The diffuse area light source 116 is separated from the transparent sheet 14 by the distance G. The distance G is between 60 cm and 125 cm and about 84 cm in a preferred embodiment. A housing 11 completely encloses the three cameras (22A, 22B, and 22C), the cross-conveyor light assembly 102, the three pairs of parallel-conveyor light assemblies (112A, 112B, and 112C), the baffles 122, and the diffuse area light source 116 and prevents ambient light from entering the housing 11.

FIG. 7 illustrates an embodiment of the present invention with three cameras (22A, 22B, and 22C) and three pairs of cross conveyor parallel-conveyor light assemblies (112A, 112B, 112C) as viewed from the top. FIG. 7 shows the relative positioning of three cameras (22A, 22B and 22C), the cross-conveyor light assembly 102, three pairs of parallel-conveyor light assemblies (112A, 112B, and 112C) and the baffles 122. The cameras (22A, 22B and 22C) and the cross-conveyor light assembly 102 are separated by a distance D. The distance D is between 20 cm and 60 cm and about 44 cm in a preferred embodiment. The cameras (22A, 22B and 22C) and the parallel-conveyor light assemblies 112 are separated by a distance E. The distance E is between 5 cm and 45 cm and about 22 cm in a preferred embodiment. The cameras (22A, 22B and 22C) are separated from each other by the distance F. The distance F is between 5 cm and 55 cm and about 30 cm in a preferred embodiment. The baffles 122 have a baffle width 123 of about 10 cm and a baffle length 125 of about 30 cm. A housing 11 completely encloses the three cameras (22A, 22B, and 22C), the cross-conveyor light assembly 102, the three pairs of parallel-conveyor light assemblies (112A, 112B, and 112C), the baffles 122, and the diffuse area light source 116 and prevents ambient light from entering the housing 11.

FIG. 8 illustrates a ray tracing of the light of the bright-field illumination as seen by the camera 22. FIG. 8 illustrates the formation of the bright-field portion of the entire image from the bright-field field of view 126. A first edge ray 130 seen by the camera 22 is directed at the center of the field of view 23 at the junction of the bright-field field of view 126 and the dark-field field of view 128. A second edge ray 132 seen by the camera 22 is at the upstream edge of the bright-field field of view 126. The second edge ray 132 entering the camera represents the first line at the top of the camera image. A housing 11 completely encloses the camera 22 and the diffuse area light source 116, preventing ambient light from entering.

FIG. 9 illustrates a top view of field of view 23 of a single camera 22. FIG. 9 shows the relative positioning of the camera 22, the cross-conveyor light assembly 102, a pair of parallel-conveyor light assemblies 112 and two baffles 122 relative to the field of view of camera 23. The camera 22 is downstream from the field of view 23 which is downstream from the cross-conveyor light assembly 102. The field of view 23 comprises a bright-field field of view 126 and a dark-field field of view 128.

FIGS. 10A-E show schematic representations of images in the camera 22 of the bright-field of view 126 and dark-field field of view 128. FIG. 10A shows a schematic representation of defects detected in the dark-field field of view 128. The white lines visible in the dark-field of view 128 are representative of typical scratches. FIG. 10B illustrates a schematic representation of a test scratch pattern under diffuse lighting. The use of diffuse light for the detection of scratches yields a low-contrast or invisible scratch pattern. FIG. 10C illustrates a schematic representation of a test scratch pattern with illumination from only the parallel-conveyor light assemblies 112. Illumination with light from the parallel-conveyor light assemblies 112 allows: the best visualization of a scratch in the parallel-conveyor orientation; some detection of a scratch oriented in both the cross-conveyor direction and the parallel-conveyor direction; and poor or no detection of a scratch oriented in the cross-conveyor direction. FIG. 10D illustrates a schematic representation of a test scratch pattern with illumination from only the cross-conveyor light assembly 102. Illumination with light from the cross-conveyor light assembly 102 allows: the best visualization of a scratch in the cross-conveyor orientation; some detection of a scratch oriented in both the cross-conveyor direction and the parallel-conveyor direction; and poor or no detection of a scratch oriented in the parallel-conveyor direction. FIG. 10E illustrates a schematic representation of a test scratch pattern with illumination from the parallel-conveyor light assemblies 112 and the cross-conveyor light assembly 102. Illumination with light from both the parallel-conveyor light assemblies 112 and the cross-conveyor light assembly 102 allows the best visualization of a scratch in all orientations: the parallel-conveyor orientation; the cross-conveyor orientation and both the parallel-conveyor orientation; and the cross-conveyor orientation. Thus, the use of light from both parallel-conveyor light assemblies 112 and the cross-conveyor light assembly 102 results in higher detection of defects on glass.

To use a glass defect detection system 10 in accordance with the present invention to inspect a transparent sheet 14, the glass defect detection system 10 may be installed on a glass production line. When installed on a glass production line, the glass defect detection system 10 is integrated into the conveyance system 12 of the line. The glass defect detection system 10 could be installed on production and inspection lines for other transparent sheets 14 including mirrored glass, acrylic, polycarbonate and other optically transparent polymer sheets.

The method according to the present invention for the examination of a transparent sheet 14 for the purpose of detecting defects in and on the transparent sheet 14 comprises: detecting a coating 15 on the transparent sheet 14 with a sensor 16, setting a sample profile for a glass defect detection system 10 based on a coating measurement from the sensor 16, transmitting the sample profile to an image processing system 26, changing inspection variables in response to the sample profile, illuminating the transparent sheet 14 with light from the illumination system 24 using inspection variables, capturing the light with an imaging device such as a camera 22 using inspection variables, transmitting an image received by the imaging device to an image processing system 26, analyzing the image for defects using inspection variables and using the results of analyzing the image for defects to accept or reject the transparent sheet 14.

As the transparent sheet 14 moves along the conveyance system 12, the sensor 16 detects the presence or absence of the coating 15 and the characteristics of the coating 15, if present, on the transparent sheet 14. The sensor is comprised of an emitter 30, an LED, and a receiver 32, an infrared sensitive photodiode, with the emitter 30 emitting at 940 nm and the receiver at 940 nm. Wavelengths in the near IR (800 to 1200 nm) or in the near ultraviolet (200-320 nm) may also be used with this invention. The infrared energy received by the receiver 32 is filtered by bandpass filter 36 and the remaining signal is converted from an analog signal to a digital signal and passed to an embedded microprocessor 38. The embedded microprocessor 38 outputs threshold values indicating which of a plurality of coatings 15 on transparent sheets 14 has been detected and the characteristics of the coatings 15, or sample profile.

As the transparent sheet 14 moves along the conveyance system 12, the illumination system 24 directs light at the transparent sheets 14 using Lumiled LED lights of 460-540 nm wavelength. A lens 25 may be used to focus the light into a semi-collimated beam. Various illumination systems may be used with this invention including the use of bright field-lighting, dark-field lighting or a combination of bright-field and dark-field lighting. Reflected light or transmitted light may also be used with this invention.

Dark-field lighting is projected onto the transparent sheet 14 and is reflected back into the camera 22 only by defects on the transparent sheet 14. The dark-field lighting is provided by a cross-conveyor light assembly 102 and pairs of parallel-conveyor light assemblies 112. The parallel-conveyor light assemblies 112 are positioned at an angle δ to the normal of the glass 114 at the center of the field of view 23 and project light onto the transparent sheet 14. The cross-conveyor light assembly 102 is positioned along an angle β to the transparent sheet 14 at the center of the field of view 23 and projects light onto the transparent sheet 14. In the absence of a defect, the light projected from the cross-conveyor light assembly 102 and parallel-conveyor light assemblies does not enter the camera 22. This is because the light is outside the field of view 23 or it is stopped by baffles 122.

Bright-field lighting is projected onto the transparent sheet 14 from a diffuse area light source 116.

As the transparent sheet 14 moves along the conveyance system 12 and passes between the conveyance system 12 and the illumination system 24, the camera 22 captures images of the light reflected by the transparent sheet 14. It is also possible with this invention for the camera 22 to capture images of transmitted light from the transparent sheet 14. A Point Gray Research area scan camera with a field of view 23 of 1600×1200 pixels is used with this invention. The camera 22 may be an area scan image device, a line scan image device or may utilize CMOS, CCD or other image sensors. Other area scan, line scan, CMOS and CCD image sensors with different sized fields of view 23 or from different manufacturers may be used with this invention.

The field of the view 23 of the camera 22 may be divided into two areas, the dark-field field of view 128 and the bright-field field of view 126. The dark-field lighting reflection is captured in the dark-field field of view 128 of the camera 22. The dark-field displays defects equally well when the defect is in a cross-conveyor orientation or parallel-conveyor orientation. The bright-field lighting reflection is captured in the bright-field field of view of the camera 22. The bright-field displays the presence and geometry of the glass, edge and shape of the glass, defects in the coating and defects included in the glass.

The images obtained by the camera 22 are transmitted to the image processing system 26. The image processing system 26 uses standard image processing techniques available in software from Open Source Computer Vision Library. Other image processing techniques may be used with this invention. The image processing system 26 outputs images to the image display 28.

As the transparent sheet 14 moves along the conveyance system 12, the encoding device 18 tracks the position of the transparent sheet 14. The encoding device 18 is a rotary encoder which pulses 2540 times per revolution of the shaft driving the belt 13 of the conveyance system 12 and is manufactured by Dynapar. Other devices for tracking the position of transparent sheets 14 along a conveyance system 12 may be used with this invention.

As the transparent sheet 14 moves along the conveyance system 12, the encoding device 18 transmits a signal to the trigger circuit 20, triggering the glass defect detection system 10 by transmitting a signal to the camera 22. The trigger circuit 20 triggers the camera 22 to capture an image about every 83.4 mm of movement of the conveyance system 12 or about every 387 pixels in the field of view 23 of the camera 22. Other conveyance system 12 distances or pixel dimensions of the field of view 23 may be used with this invention.

The foregoing discussion discloses and describes merely exemplary embodiments of the present invention. The invention is not limited to the method and the apparatus for inspection as described in the detail above. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. A glass defect detection system, for the inspection of a large optically transparent sheet for the purpose of detecting defects in and on the transparent sheet, comprising:

a plurality of illumination sources
for projecting light onto the transparent sheet where each of the plurality of illumination sources comprise: a dark-field light assembly comprising a cross-conveyor light assembly and a plurality of parallel-conveyor light assemblies;
a plurality of baffles;
a plurality of imaging devices
for receiving light reflected and scattered from the transparent sheet, providing an image of the transparent sheet and transmitting the image of the transparent sheet to an image processing system, and;
an image processing system
for analyzing the image for the defects in and on the transparent sheet.

2. The glass defect detection system, as in claim 1, wherein each of the plurality of imaging devices has a field of view comprising a dark-field field of view, and each of the plurality of baffles is positioned relative to each of the plurality of imaging devices and the dark-field light assembly to prevent light from the dark-field light assembly from reflecting off the transparent sheet, such that a reflected image of each of the plurality of illumination sources does not appear in the field of view of each of the plurality of imaging devices.

3. The glass defect detection system, as in claim 1, wherein each of the plurality of illumination sources produces a semi-collimated beam positioned at an angle beta to a normal of the transparent sheet, and a reflection of the semi-collimated beam from the transparent sheet is located outside a field of view of each of the plurality of imaging devices, and each of the plurality of imaging devices is positioned at an angle alpha to a normal of the transparent sheet and the difference in the angle alpha and the angle beta is less than forty-five degrees.

4. The angles alpha and beta, as in claim 3, wherein the angles alpha and beta are less than thirty degrees from the normal of the transparent sheet.

5. The glass defect detection system, as in claim 1, wherein each of the plurality of illumination sources and each of the plurality of imaging devices are on a same side of the transparent sheet.

6. The glass defect detection system, as in claim 1, wherein the cross-conveyor light assembly and each of the plurality of parallel-conveyor light assemblies are linear arrays of LEDs.

7. A glass defect detection system, for the inspection of a large transparent sheet for the purpose of detecting defects in and on the transparent sheet, comprising:
a plurality of illumination sources
for projecting light onto the transparent sheet where each of the plurality of illumination sources comprise: a dark-field light assembly comprising a cross-conveyor light assembly and a plurality of parallel-conveyor light assemblies; and a bright-field light assembly;
a plurality of baffles;
a plurality of imaging devices
for receiving light reflected and scattered from the transparent sheet, providing an image of the transparent sheet and transmitting the image of the transparent sheet to an image processing system, where each of the plurality of imaging devices is an area scan camera, and;
an image processing system
for analyzing the image for the defects in and on the transparent sheet.

8. The glass defect detection system, as in claim 7, wherein the camera has a field of view comprising a dark-field field of view and a bright-field field of view, and each of the plurality of baffles is positioned relative to each of the plurality of imaging devices and the dark-field light assembly to prevent light from the dark-field light assembly from reflecting off the transparent sheet, such that a reflected image of each of the plurality of illumination sources does not appear in the field of view of the camera.

9. The glass defect detection system, as in claim 7, wherein the dark-field light assembly produces a semi-collimated beam positioned at an angle beta to a normal of the transparent sheet, and a reflection of the semi-collimated beam from the transparent sheet is located outside a field of view of the camera, and the camera is positioned at an angle alpha to a normal of the transparent sheet and a difference in the angle alpha and the angle beta is less than forty-five degrees.

10. The angles alpha and beta, as in claim 9, wherein the angles alpha and beta are less than thirty degrees from the normal of the transparent sheet.

11. The glass defect detection system, as in claim 7, wherein each of the plurality of illumination sources and the camera are on a same side of the transparent sheet.

12. The bright-field light assembly, as in claim 7, wherein a reflection of light from the bright-field light assembly is detected by the camera in a bright-field field of view and can be used to determine a presence and a geometry of the transparent sheet.

13. The glass defect detection system, as in claim 7, wherein the camera receives light from the bright-field light assembly and the dark-field light assembly simultaneously.

14. The glass defect detection system, as in claim 7, wherein the cross-conveyor light assembly and each of the plurality of parallel-conveyor light assemblies are linear arrays of LEDs.

15. A method for the optical inspection of a large transparent sheet for the purpose of detecting defects in and on the large transparent sheet, comprising:
projecting light onto the transparent sheet from a plurality of illumination sources where each of the plurality of illumination sources comprise: a dark-field light assembly comprising a cross-conveyor light assembly and a plurality of parallel-conveyor light assemblies;
blocking light reflected from the transparent sheet with a plurality of baffles;
receiving light in an imaging device that provides an image of the transparent sheet and transmitting the image of the transparent sheet to an image processing system; and
analyzing the image for the defects with the image processing system.

16. The method in claim 15, characterized in that receiving light in an imaging device includes receiving light from a dark-field field of view, and blocking light requires the positioning of baffles relative to the imaging device and the dark-field light assembly, so that a reflected image of each of the plurality of illumination sources does not appear in a field of view of the imaging device.

17. The method in claim 15, characterized in that in projecting light, the dark-field light assembly produces a semi-collimated beam positioned at an angle beta to a normal of the transparent sheet, with a reflection of the semi-collimated beam from the transparent sheet located outside a field of view of the imaging device, with the imaging device positioned at an angle alpha to a normal of the transparent sheet and a difference in the angle alpha and the angle beta is less than forty-five degrees.

18. The method as in claim 17, characterized in that the angle alpha and the angle beta are less than thirty degrees from the normal of the transparent sheet.

19. The method as in claim 15, characterized in that projecting light and receiving light occur on a same side of the transparent sheet.

20. The method as in claim 15, characterized in that projecting light further comprises projecting light with a bright-field light assembly.

21. The method as in claim 15, characterized in that in projecting light the cross-conveyor light assembly and each of the plurality of parallel-conveyor light assemblies are linear arrays of LEDs.

22. The method as in claim 15, characterized in that in receiving light, the imaging device is an area scan camera.

* * * * *